United States Patent [19]

Choi et al.

[11] Patent Number: 5,032,628

[45] Date of Patent: Jul. 16, 1991

[54] PROCESS FOR THE PREPARATION OF A HIGHLY WATER ABSORPTIVE RESIN FROM ACRYLIC RESIN, EPOXY CROSSLINKER AND HYDROPHILIC SILICATE

[75] Inventors: Su B. Choi; Hyung M. Lee, both of Daejeon, D.P.R. of Korea

[73] Assignee: Lucky, Ltd., Seoul, Rep. of Korea

[21] Appl. No.: 349,172

[22] Filed: May 9, 1989

[30] Foreign Application Priority Data

May 13, 1988 [KR] Rep. of Korea ............... 88-5570

[51] Int. Cl.$^5$ ............................................ C08L 63/00
[52] U.S. Cl. .................................... 523/409; 523/412; 525/119; 524/493
[58] Field of Search ............... 523/409, 412; 525/119

[56] References Cited

U.S. PATENT DOCUMENTS

| | | | |
|---|---|---|---|
| 3,926,891 | 12/1975 | Gross et al. | 523/412 |
| 3,966,679 | 6/1976 | Gross | 525/107 |
| 4,061,846 | 12/1977 | Gross et al. | 525/119 |
| 4,076,663 | 2/1978 | Masuda et al. | 260/17.4 |
| 4,093,776 | 6/1978 | Aoki et al. | 428/402 |
| 4,340,706 | 7/1982 | Obayashi et al. | 525/383 |
| 4,351,922 | 9/1982 | Yoshida et al. | 525/116 |
| 4,446,261 | 1/1984 | Yamasaki et al. | 524/40 |
| 4,497,930 | 2/1985 | Yamasaki et al. | 524/556 |
| 4,507,438 | 3/1985 | Obayashi et al. | 525/119 |
| 4,541,871 | 9/1985 | Obayashi et al. | 525/119 |
| 4,666,975 | 5/1987 | Yamasaki et al. | 525/119 |
| 4,666,983 | 5/1987 | Tsubakimoto et al. | 525/119 |
| 4,727,097 | 2/1988 | Kobayashi et al. | 523/409 |
| 4,806,578 | 2/1989 | Kobayashi et al. | 523/402 |

*Primary Examiner*—Earl A. Nielsen
*Assistant Examiner*—Frederick Krass
*Attorney, Agent, or Firm*—Birch, Stewart, Kolasch & Birch

[57] ABSTRACT

A method for the production of a highly water absorptive resin comprises the steps of neutralizing acrylic acid with alkali metal hydroxide to form an alkali metal acrylate; mixing the alkali metal acrylate, methacrylic acid, a polymerization initiator, and a first crosslinking agent; suspending and dispersing the mixture in an aqueous medium to for an initial mixture; polymerizing the initial mixture to produce a polymerized intermediate, and separating the moisture from the polymerized intermediate by azeotropic distillation to reduce the water content to 15-35% by weight; adding a second crosslinking agent, said second crosslinking agent having two epoxy radicals; and mixing "Syloid" of silicate, to form a highly water absorptive resin.

7 Claims, No Drawings

PROCESS FOR THE PREPARATION OF A HIGHLY WATER ABSORPTIVE RESIN FROM ACRYLIC RESIN, EPOXY CROSSLINKER AND HYDROPHILIC SILICATE

BACKGROUND OF THE INVENTION

1. Field of the Invention

The present invention relates to a process for the preparation of a highly water absorptive resin and more particularly, to a process for producing a highly water absorbing resin having a high water absorption rate, and an excellent gel strength and fluidity and its manufacture.

2. Description of the Prior Art

Various water absorbing materials such as natural sponge, pulp, paper and the like, are well known in the art. Also various synthetic products made by graft polymerization of materials having a water absorbing group, such as —OH, —NH$_2$, —COOH, and the like, have been used conventionally. However, such water absorbing natural materials, e.g. a sponge, a pulp, a paper are characterized with physical mechanism for absorbing water so that such materials have defects in that the majority of the absorbed water can be easily squeezed out by the application of external pressure. In recent years, in order to solve these defects, the synthetic products having particular physical and chemical mechanisms have been developed. The majority of such synthetic water absorptive products are crosslinked polyacrylic acid salt, or polymethacrylic acid salt, crosslinked polyarcylic acid-methacrylic acid copolymer, salt, crosslinked starch-acrylonitrile graft copolymer, and cellulose and acrylate-grafted copolymer. Such grafted products are on the market as sanitary napkins, sanitary pads, diapers in the sanitary field, water absorbing containers in the civil and gardening field, and anti-dewdrop agents in the construction field.

The processes for the preparation of these products are shown in U.S. Pat. No. 4,076,663 which discloses a process comprising graft polymerization of starch and acrylic acid, and hydrolyzing the starch-polyacryl-grafted polymer, and U.S. Pat. No. 4,093,776 which discloses a process comprising the polymerization carried out by suspending and dispersing an aqueous solution of crosslinked sodium polyacrylate. However, the products made by these processes have a lower water absorbing property so that these products are not properly utilized as sanitary pads or paper diapers.

In general, a high water absorptive resin requires water absorption rate, water absorptive capacity, and gel strength and they have mutual opposing properties with each other. On the other hand, each performance is sacrificed to some extent. For example, the sanitary pads or paper diapers require a high absorption capacity as well as a high water absorption rate because the liquid from the human body can contact the human skin so that skin diseases such as edema, dermatitis, or congestive skin are formed on the human skin. Furthermore, the water content can be leaked from the water absorptive products. Accordingly, the necessity of good products for desired pads or diapers requires that there are to be several types of water absorptive resins which are known in the art. One such water absorptive resin is shown in U.S. Pat. No. 4,497,930 which discloses a process for producing a water absorbent polymer comprising the steps of subjecting a crosslinked sodium polyacrylate to have a water content of 10 to 40% wt, and adding a crosslinking agent for crosslinking the surface thereof. However, such water absorptive resin has a insufficient water absorptive property and a lower gel strength.

SUMMARY OF THE INVENTION

Accordingly, it is an object of the present invention to provide an improved process for the preparation of a highly water absorptive resin having a high water absorption rate, as well as having an excellent gel strength and fluidity.

Another object of the present invention is to provide a process for producing a highly water absorbing resin which comprises enlarging the size of the particles thereof by adding methacrylic acid as a reaction buffer agent and further adding "Syloid", a type of hydrophilic silicates to produce a water absorptive resin which has an excellent gel strength, a high water absorption capacity and a high water absorption rate. By "hydrophilic silicates" we mean silicon dioxide hydrates of the series having the general formula (SiO$_2$.$n$-H$_2$O), where n is a positive integer, hereinafter also referred to as a "Syloid" or one of the "silicate series."

A further object of the present invention is to provide a process for producing a highly water absorptive resin which comprises the steps of neutralizing 50-100 mol percent of acrylic acid with an alkali metal hydroxide to produce an equivalent amount of an alkali metal acrylate having the degree of neutralization of 50-100 mol percent; mixing 70-90% by weight of the produced alkali metal acrylate, 10-30% by weight of methacrylic acid, a water soluble radical polymerization initiator, and a first crosslinking agent; suspending and dispersing the initial mixture in an aqueous medium and inversely polymerizing the initial mixture so constructed to form a polymerized intermediate; removing the moisture from the polymerized intermediate by azeotropic distillation to reduce the water content of the polymerized intermediate to about 15-35% by weight; said polymerized intermediate having an average particle size of about 100-150 $\mu$m. Adding 1.2-8% by weight of a second crosslinking agent, said second crosslinking agent having at least two epoxy radicals based on the polymerized intermediate for increasing the density of the surface thereof; and mixing 0.1-5% by weight of "Syloid", one of the silicate series, based on the polymerized intermediate to produce a highly water absorptive resin.

Other objects and further scope of applicability of the present invention will become apparent from the detailed description given hereinafter. It should be understood, however, that the detailed description and specific examples, while indicating preferred embodiments of the invention, are given by way of illustration only, since various changes and modifications within the spirit and scope of the invention will become apparent to those skilled in the art from this detailed description.

Briefly described, the present invention is directed to a method for the production of a highly water absorptive resin which comprises the steps of neutralizing acrylic acid with an alkali metal hydroxide; mixing the alkali metal acrylate, methacrylic acid, a polymerization initiator, and a first crosslinking agent; polymerizing the initial mixture in a water suspension to produce an intermediate, and separating the moisture from the intermediate by the azeotropic distillation to reduce the water content to 15-35% by weight; adding a second crosslinking agent said second crosslinking agent, surface crosslinking agent, having at least two epoxy radicals; and mixing "Syloid" (a silicate) to form a highly water absorptive resin and the present invention is also directed to a product produced by the method.

DESCRIPTION OF PREFERRED EMBODIMENTS

Referring now in detail to the present invention, there is provided a highly water absorptive resin having a highly gel strength and fluidity and a process for its manufacture.

The present invention is directed to a process for the preparation of a highly water absorptive resin which comprises the steps of (a) neutralizing 50-100 mol percent of acrylic acid with an alkali metal hydroxide to produce an equivalent amount of an alkali metal acrylate; (b) mixing about 70-90% by weight of the produced alkali metal acrylate of step (a), about 10-30% by weight of methacrylic acid, a polymerization initiator, and a first crosslinking agent; (c) suspending and dispersing the initial mixture in an aqueous medium and polymerizing the initial mixture so constructed to form a polymerized intermediate; (d) separating the moisture from the polymerized intermediate by azeotropic distillation to reduce the water content of the polymerized intermediate to about 15-35% by weight, said polymerized intermediate having an particle size of about 100-150 $\mu$m; (e) adding about 1.2-8% by weight of the second crosslinking agent, said second crosslinking agent having at least two epoxy radicals based on the polymerized intermediate for increasing the density of the surface thereof; and (f) mixing about 0.1-5% by weight of "Syloid", one of the silicate series, based on the polymerized intermediate to produce a highly water absorptive resin.

The alkali metal acrylate can be obtained by reacting acrylic acid with an alkali metal hydroxide such as lithium hydroxide, sodium hydroxide, potassium hydroxide and calcium hydroxide. The preferred degree of neutralization is about 5-100 mol percent and the more preferred degree of neutralization is about 65-80 mol percent. When the neutralization degree is lower than 50% mol, the hydroxide concentration would be decreased and the electronic density in the water would also be small and further, the penetration intensity would be decreased. Thus the desired highly water absorptive resin would not be obtainable. The concentration of the monomer, thus produced, i.e., the alkali metal acrylate and the unreacted acrylic acid, is about 20-70% by weight based on the total weight of the composition and the preferred monomer concentration is about 40-60% by weight.

The crosslinking agents according to the present invention can be classified the (b) step first crosslinking agent and the (e) step second crosslinking agent. The first crosslinking agent is preferably N,N-methylene bisacrylamide and the second crosslinking agent, a surface crosslinking agent, is one having at least two epoxy groups wherein the group presents in the polymer such as hydroxy group, sulfonic group, amino group, and the like, or any crosslinking agent having at least two functional groups which are reacted with the carboxylate.

Examples of the second crosslinking agent to be used in the present invention are polyethylene glycol diglycidyl ether, ethylene glycol diglycidyl ether, polypropylene glycol diglycidyl ether, polyglycerin diglycidyl ether, glycerin diglycidyl ether, glycerol polyglycidyl ether, haloepoxy compounds such as epichlorohydrin, epibromohydrin, and α-methyl epichlorohydrin, aldehyde compounds such as glutaraldehyde and glyoxal, isocyante compounds such as 2,4-tolylene diisocyanate, hexamethylene diisocyanate. 1.2-8% by weight of the ethylene glycol diglycidyl ether or glycerol polyglycidyl ether is more preferably used in the present invention. When the second crosslinking agent is less than 1.2% by weight, it decreases the effect of surface crosslinking and the water absorption rate is decreased. But, when the crosslinking agent is over 8% by weight, the water absorptive capacity is decreased.

When the methacrylic acid in (b) step is less than 10% by weight, it is decreased the effect of surface crosslinking since the particle size is too small but, when the methacrylic acid is over 30% by weight, the water absorptive rate is decreased since the particle size is too large. Examples of the solvents according to the process of the present invention, are n-hexane, n-heptane, cyclohexane, and the like. The preferred solvent is the cyclohexane.

In (d) step, methanol is used for improving the surface treatment. At this time, when the water content is 15% by weight, it is uneconomic but, when the water content over 35% by weight, it cannot achieve the effect of surface crosslinking. When the particle size is less than 100 $\mu$m, it is decreased the effect of surface crosslinking but, when the particle size is over 150 $\mu$m, the water absorptive rate is decreased.

In (b) step, the polymerization initiator is ammonium persulfate, potassium persulfate, hydroperoxide. It is preferred to add a dispersing agent such as sorbitol monolauylate, ethyl cellulose, or carboxymethyl cellulose. The more preferred is ethyl cellulose.

The "Syloid ($SiO_2 \cdot nH_2O$)" made by Fuji Davison Chemical Ltd (620 grade) in (f) step is a type of silicate which has a hydroxy radical on the surface thereof. The "Syloid" particle has a diameter of 10-20 $\mu$m and a surface square of 300 mm$^2$/g. The "Syloid" may be used in the quantity of about 0.1-5% by weight. When the amount of "Syloid" is less than 0.1% by weight, it cannot involve the effect of the process according to the present invention. When the amount of "Syloid" is over 5% by weight, result would be unchanged from a use of 0.1-5% by weight of the "Syloid". Accordingly, it is not economic to use an amount of over 5% by weight of the "Syloid" in the reaction according to the present invention.

According to the present invention, the process for the preparation of the highly water absorptive resin in detail is as follows:

(a) Step: Process of Neutralizing

Acrylic acid is charged in a reactor equipped with a condenser, a dropping funnel, and a stirrer. An alkali metal hydroxide is dissolved in water in a beaker separately to form an alkali metal hydroxide. The alkali metal hydroxide solution is fed dropwise to the reactor through the dropping funnel while being kept at less than 30° C. and neutralizing 50-100 mol percent of the acrylic acid to produce an equivalent amount of an alkali metal acrylate having the degree of neutralization of 50-100 mol percent. When the neutralization step is conduct at a temperature of over 45° C., one of reactants could be polymerized.

(b) Step: Process of Mixing

Dispersing agent and solvent are charged in a reactor equipped with a stirrer, a reflux condenser, a dropping funnel, and nitrogen gas inlet pipe while being maintained at a temperature of 35°-80° C. The produced alkali metal acrylate of step (a), methacylic acid and the first crosslinking agent are added to the reactor to form a mixture. Thereafter, a polymerization initiator is added to the mixture forming an initial mixture.

(c) Step: Process of Polymerizing

The initial mixture in the reactor is suspended and dispersed in an aqueous medium and is polymerized at a temperature in the range of from 75°-100° C. for 10-60 minutes to form a polymerized intermediate.

(d) Step: Process of Azeotropic Distilling

The polymerized intermediate contains a large amount of water so that it is difficult for the second crosslinking agent to react with the polymer in (c) step. Therefore, the moisture contained in the polymerized intermediate is separated therefrom by azeotropic distillation at a temperature of 80° C. in the din-stack apparatus which reduces the water content of the polymerized intermediate to 15-35% by weight.

(e) Step: Process of Surface Crosslinking

The water content adjusted polymerized intermediate produced by (d) step is crosslinked by the second crosslinking agent so as to improve water absorptive rate and gel strength. The intermediate polymer and methanol, in an amount of 2-5 times the amount of the polymer, are charged to a reactor equipped with a condenser, stirrer, a dropping funnel, while being maintained at a temperature of 70° C. The second crosslinking agent, in an amount of 1.2-8% by weight based on the weight of the polymer, is added to the reactor over a period of 2 hours for crosslinking surface treatment. The so treated polymer is filtered and dried at a temperature of 80°-100° C. for 2-4 hours in a vacuum dryer.

(f) Step: Process of Mixing with Silicate

Usually, the polymer produced by (e) step has sticky characteristics so that its water absorption rate may be decreased, and its particles are closely banded together and thus does not have the necessary fluidity so as to not enable one to use it without a great amount of difficulty. Accordingly, "Syloid" which is a type of silicate, which has a OH radical disposed thereon is added to the polymer. The amount of "Syloid" added is from 0.1-5% by weight based on the polymer which is used for producing the highly water absorptive resin.

The present invention will now be described in more detail in connection with the following examples which should be considered as being exemplary and not be considered as limiting the present invention.

EXAMPLE 1

250 g of cyclohexane and 2.5 g of ethyl cellulose (ethoxyl content 40% wt) are charged in a 1 l four-necked round-bottomed flask (A) equipped with a stirrer, din-stack condenser, pressure adjusting dropping funnel, and nitrogen gas inlet pipe. And the nitrogen is introduced into the flask so as to exhaust oxygen in the flask and are heated to 67° C.

Separately, 36 g of acrylic acid is neutralized by 15 g of sodium hydroxide dissolved in 50 g of distilled water in a 1 l four-necked round-bottomed flask (B) equipped a stirrer, condenser, and a dropping funnel. 0.04 g of bisacrylamide is added to flask (B). The monomer concentration is 45% by weight.

10 g of methacrylic acid is added to the alkali metal acrylate in flash (B) while being stirred. After 0.03 g of potassium persulfate and 10 g of distilled water are separately charged to a 100 ml beaker to form a solution, the solution is added to the alkali metal acrylate and methacrylic acid mixture in flask (B). The nitrogen gas is introduced into flask (B) so as to exhaust oxygen therein. The solution in flask (A) is slowly fed dropwise to the mixture in flask (B) through the pressure adjusting dropping funnel for 30 minutes to conduct a polymerization reaction. Thereafter, the polymerization reaction mixture in flask (B) is held at a temperature of 70° C. for 3 hours to complete the polymerization. At this time, the temperature is increased to a temperature of 80° C. to separate 51.7 g of water from the polymer by azeotropic distillation to reduce the water content to about 20% by weight. And the resulting polymer is filtered and dried and, the cyclohexane is removed. At this time, 69.33 g of the highly water absorptive resin intermediate is obtained.

69.33 g of the produced resin is charged in a 1 l flask (C) and 200 g of methanol is added to the resin in flask (C). 0.5 g of ethylene glycol diglycidyl ether dissolved in 5 g of distilled water and 5 g of methanol are added to the resin solution in flask (C) while being maintained at a temperature of 70° C. for 2 hours. After the reaction is completed, the flask (C) is cooled at room temperature, filtered, and dried at a temperature of 80° C. and a reduced pressure for 4 hours to produce 69.83 g of resin. The produced resin is pulverized as a unified size of 80 mesh. At this time, 1.4 g of "Syloid" is added to the pulverized resin to finally produced a highly water absorptive resin.

EXAMPLE 2

A highly water absorptive resin is prepared in the same manner as described in Example 1 except that 1.5 g of ethylene glycol diglycidyl ether is added as the second crosslinking agent.

EXAMPLE 3

A highly water absorptive resin is prepared in the same manner as described in Example 1 except that 0.5 g of "Epok" 812 is used instead of 0.5 g of ethylene glycol diglycidyl ether.

EXAMPLE 4

A highly water absorptive resin is prepared in the same manner as described in Example 1 except that 0.5 g of "Epok" 812 is used instead of 1.5 g of ethylene glycol diglycidyl ether.

COMPARATIVE EXAMPLE 1

A water absorptive resin is prepared in the same manner as described in Example 1 except that the second crosslinking agent in (e) step is not use and also the "Syloid" in (f) step is not used.

COMPARATIVE EXAMPLE 2

A water absorptive resin is prepared in the same manner as described in Example 1 except that the "Syloid" in (f) step is not used.

COMPARATIVE EXAMPLE 3

A water absorptive resin is prepared in the same manner as described in Example 2 except that the "Syloid" in (f) step is not used.

COMPARATIVE EXAMPLE 4

A water absorptive resin is prepared in the same manner as described in Example 3 except that the second crosslinking agent in (e) step is not used and also the "Syloid" in (f) step is not used.

COMPARATIVE EXAMPLE 5

A water absorptive resin is prepared in the same manner as described in Example 4 except that the "Syloid" in (f) step is not used.

The highly water absorptive resin obtained in Example 1–4 and Comparative Examples 1–5 is illustrated in Table I as follows:

TABLE I

|  | Absorption rate in 0.9% NaCl aqueous solution (g/g polymer) | | | | |
| --- | --- | --- | --- | --- | --- |
|  | 1 min | 3 min | 5 min | gel-strength | fluidity |
| Example 1 | 40 | 47 | 45 | ○ | ○ |
| Example 2 | 40 | 47 | 47 | ○ | ○ |
| Example 3 | 46 | 51 | 50 | ○ | ○ |
| Example 4 | 46 | 52 | 51 | ○ | ○ |
| C. Example 1 | 10 | 31 | 50 |  |  |
| C. Example 2 | 25 | 50 | 50 | ○ |  |
| C. Example 3 | 23 | 47 | 47 | ○ |  |
| C. Example 4 | 26 | 50 | 50 | ○ |  |
| C. Example 5 | 28 | 52 | 52 | ○ |  |

*○: excellent
 : normal
 : poor

As shown in above Table I, the absorption rate, gel-strength, and fluidity properties of the resin according to the present invention are an improvement as when compared with those having been prepared by prior art processes.

The invention being thus described, it will be obvious that the same may be varied in many ways. Such variations are not to be regarded as a departure from the spirit and scope of the invention, and all such modifications as would be obvious to one skilled in the art are intended to be included in the scope of the following claims.

What is claimed is:

1. A process for preparing a highly water absorptive resin comprising the steps of:

(a) neutralizing crylic acid with an alkali metal hydroxide to produce an equivalent amount of alkali metal acrylate;

(b) mixing about 70–90% by weight of the produced alkali metal acrylate of step (a), about 10–30% by weight of methacrylic acid, a polymerization initiator, and a first crosslinking agent comprising N,N-methylene bisacrylamide to form an initial mixture;

(c) dispersing the initial mixture in an aqueous medium and polymerizing the dispersed initial mixture to form a polymerized intermediate aqueous dispersion;

(d) removing the water from the polymerized intermediate aqueous dispersion by azeotropic distillation to reduce the water content of the polymerized intermediate aqueous dispersion to about 15–35% by weight, wherein said polymerized intermediate comprised in the aqueous dispersion has an average particle size of about 100–150 $\mu$m;

(e) adding about 1.2–8% by weight based on the weight of the polymerized intermediate of a second crosslinking agent, said second crosslinking agent having at least two epoxy radicals for increasing the density of the surface thereof; and (f) mixing about 0.1–5% by weight of a silicon dioxide hydrate ($SiO_2 \cdot {}_nH_2O$) wherein n is a positive integer based on the polymerized intermediate to produce a highly water absorptive resin.

2. The process of claim 1, wherein the second crosslinking agent having at least two epoxy radicals is selected from the group consisting of polyethylene glycol diglycidyl ether, ethylene glycol diglycidyl ether, polypropylene glycol diglycidyl ether, polyglycerin diglycidyl ether, glycerin diglycidyl ether, and glycerol polyglycidyl ether.

3. The process of claim 1, wherein the second crosslinking agent having at least two epoxy radicals of step (e) is selected from the group consisting of ethylene glycol diglycidyl ether and glycerol polyglycidyl ether.

4. The process of claim 1, wherein the particle of the silicon dioxide hydrate has a diameter of 10–20 $\mu$m and a surface of 300 $mm^2/g$.

5. The process of claim 1, wherein the alkali metal hydroxide is selected from the group consisting of lithium hydroxide, sodium hydroxide, potassium hydroxide and calcium hydroxide.

6. The process of claim 1, wherein the alkali metal acrylate is selected from the group consisting of lithium acrylate, sodium acrylate, potassium acrylate and calcium acrylate.

7. The process of claim 1, wherein 50 to 100 mol percent of acrylic acid is neutralized to convert it to the equivalent amount of the alkali metal acrylate in step (a).

* * * * *

UNITED STATES PATENT AND TRADEMARK OFFICE
CERTIFICATE OF CORRECTION

PATENT NO. : 5,032,628
DATED : July 16, 1991
INVENTOR(S) : Su B. Choi and Hyung M. Lee It is certified that error appears in the above-identified patent and that said Letters Patent is hereby corrected as shown below:

ON TITLE PAGE: Item "[75] Inventors:", please change

"D.P.R. of Korea" to --Republic of Korea--.

Signed and Sealed this

Twelfth Day of January, 1993

Attest:

DOUGLAS B. COMER

*Attesting Officer*      *Acting Commissioner of Patents and Trademarks*